(12) United States Patent
Coleman et al.

(10) Patent No.: US 8,268,629 B2
(45) Date of Patent: Sep. 18, 2012

(54) METHOD FOR THE MEASUREMENT OF WATER AND WATER-SOLUBLE COMPONENTS IN NON-AQUEOUS LIQUIDS

(75) Inventors: Thomas Coleman, Yakima, WA (US);
Frederick Wolf, Seattle, WA (US);
James E Bruya, Seattle, WA (US)

(73) Assignee: dTEC Systems L.L.C., Seattle, WA (US)

( * ) Notice: Subject to any disclaimer, the term of this patent is extended or adjusted under 35 U.S.C. 154(b) by 1601 days.

(21) Appl. No.: 11/156,714

(22) Filed: Jun. 21, 2005

(65) Prior Publication Data

US 2006/0286675 A1    Dec. 21, 2006

(51) Int. Cl.
*G01N 33/00*    (2006.01)

(52) U.S. Cl. ........ 436/139; 436/147; 436/148; 436/149; 436/150; 73/64.43; 73/64.44; 73/64.45; 73/64.46; 73/64.47; 73/29.01; 73/335.01; 422/82.01; 422/82.02

(58) Field of Classification Search ............... 422/82.01, 422/82.02; 436/2, 39, 40, 60, 149, 150, 139, 436/147–148; 73/29.02, 29.01, 335.01, 335.05, 73/64.43–64.47
See application file for complete search history.

(56) References Cited

U.S. PATENT DOCUMENTS

| | | | |
|---|---|---|---|
| 2,760,368 A | * | 8/1956 | Coffman .................... 73/61.43 |
| 5,179,926 A | * | 1/1993 | Ament ......................... 123/494 |
| 6,377,052 B1 | | 4/2002 | McGinnis et al. |
| 6,664,796 B2 | | 12/2003 | Wang et al. |

FOREIGN PATENT DOCUMENTS

WO    WO 86/03043    *    6/1986

OTHER PUBLICATIONS

French R et al: Fluid Phase Equilibria, Elsevier, vol. 228-229, Feb. 2005, pp. 27-40, XP004870767, ISSN: 0378-3812.
Karaosmanoglu F et al : Journal of the Institute of Energy, Institute of Energy, London, GB, vol. 61, No. 448, 1988, pp. 125-128, XP002965856, ISSN: 0144-2600.

* cited by examiner

*Primary Examiner* — Lyle Alexander

(57) ABSTRACT

A system and method for characterizing a liquid hydrocarbon fuel having unknown or variable composition is described and shown herein.

7 Claims, 3 Drawing Sheets

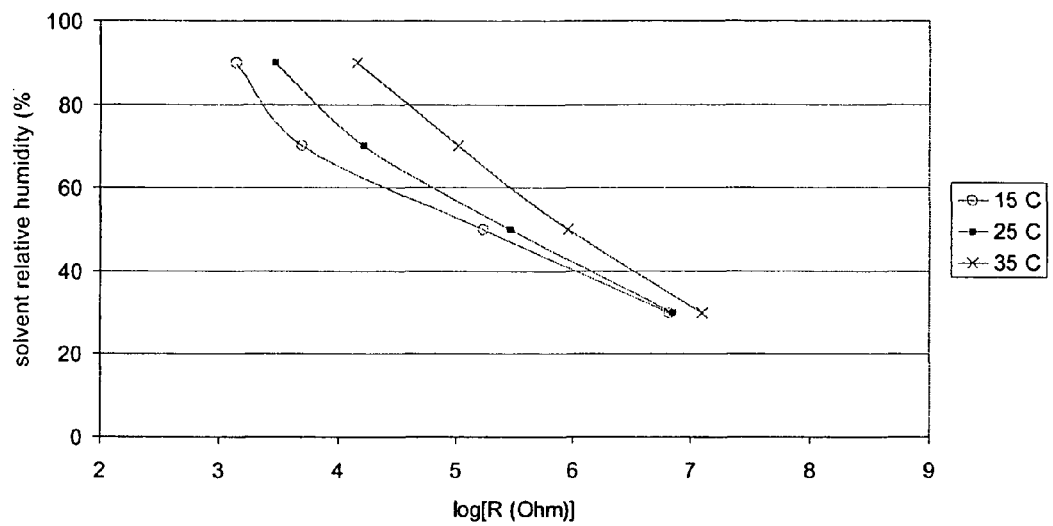
Figure 1: EMD3000 response in unoxygenated gasoline
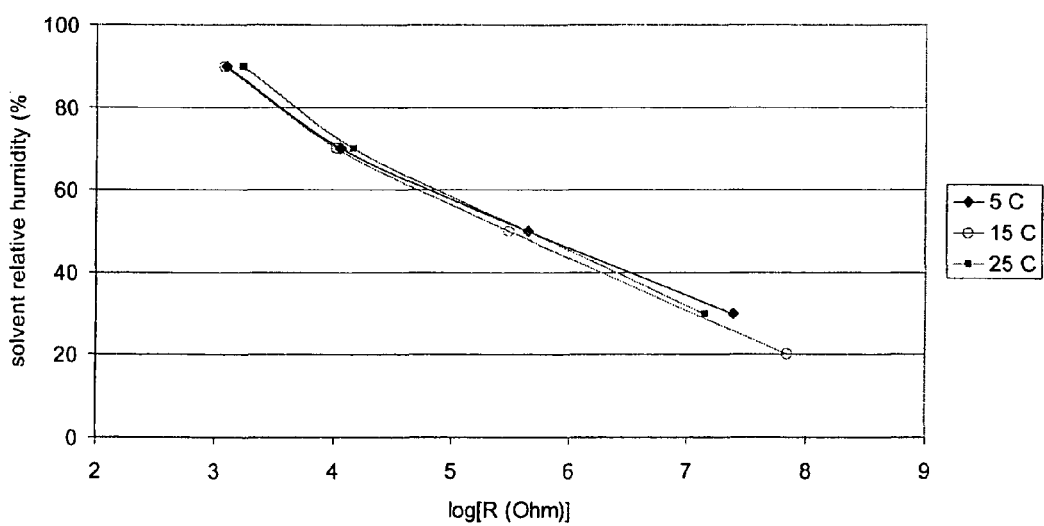
Figure 2: EMD3000 response in 11% MTBE containing gasoline

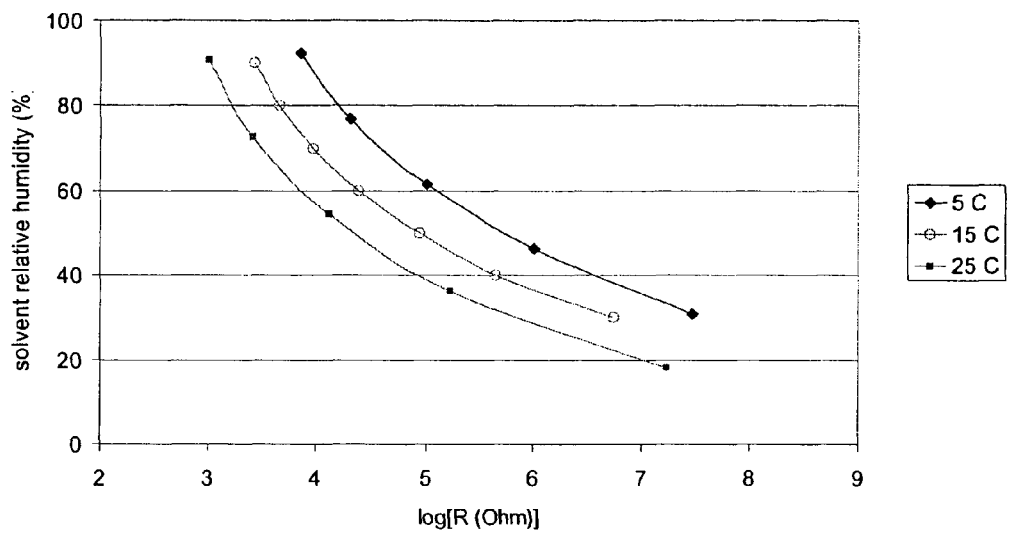
Figure 3: EMD3000 response in 10% ethanol containing gasoline
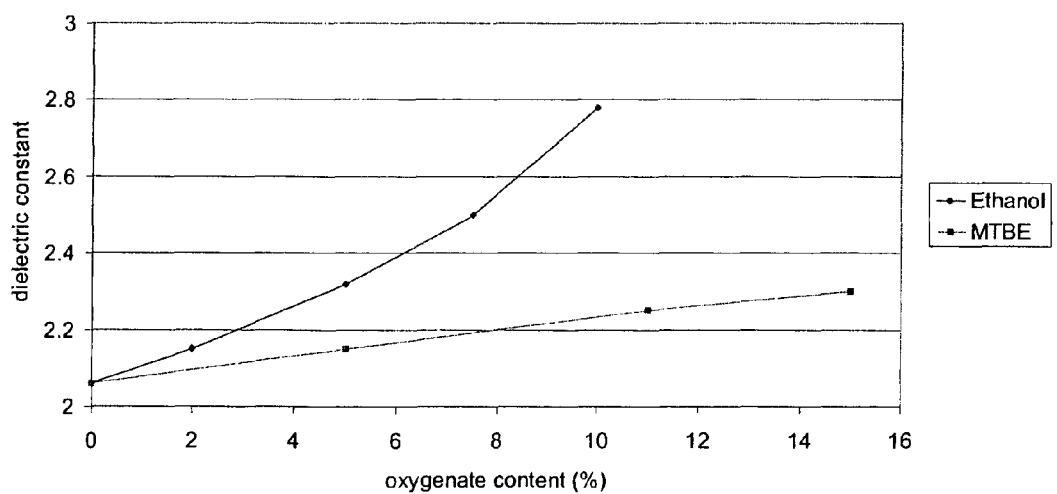
Figure 4: The relationship between oxygenate content and the dielectric constant, 20C

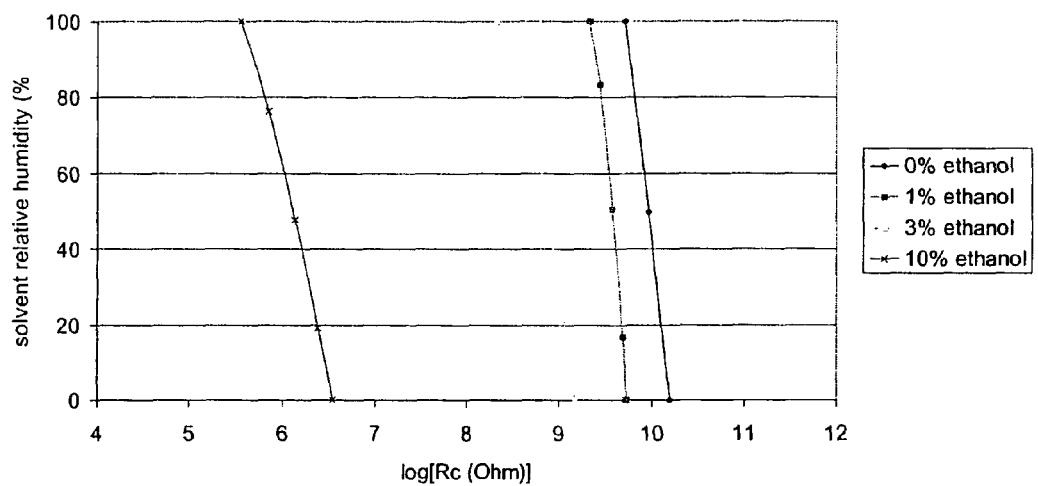
Figure 5: A depiction of the relationship between ethanol content of gasoline, solvent relative humidity, and bulk electrical resistance, 20C
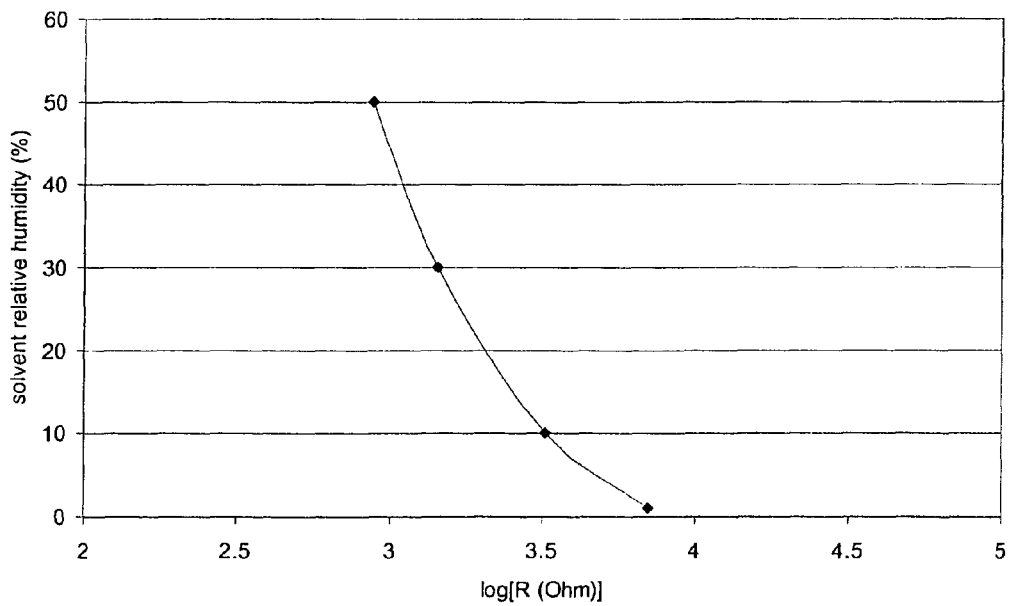
Figure 6: EMD4000 response in ethyl alcohol

METHOD FOR THE MEASUREMENT OF WATER AND WATER-SOLUBLE COMPONENTS IN NON-AQUEOUS LIQUIDS

BACKGROUND OF THE INVENTION

It has long been difficult to determine the quality of liquid fuels during transportation and storage. This has especially been true due to the presence of water or water-soluble components in non-aqueous liquid fuels, as the potential for water or water-soluble components to cause harm may be less dependent upon the amount of such components which are present than upon the conditions of transportation and storage.

Conventional methods for measuring water content within non-aqueous liquids usually fall into two categories, quantitative methods that require expensive equipment and labor, and simple methods that yield highly qualitative results. The quantitative approaches include analytical laboratory equipment and industry specific analyzers. While water-cut analyzers have been developed for the crude oil industry, these instruments are designed to measure water present in a separate phase from the crude oil. Simple methods, such as color changing indicator chemicals, may be highly portable and easy to use, but may not provide the information desired.

The conventional laboratory-based method for the measurement of water dissolved within non-aqueous liquids is Karl Fischer titration (see ASTM D 1744). While very accurate, the use of the Karl Fischer titration requires an expensive piece of equipment, the Karl Fischer titrator, and a trained technician as operator. In a facility or transport setting, standard analytical equipment is expensive, complicated, fragile, maintenance intensive, and requires trained technicians. Additionally, in a field setting, the instrument machinery may not be sufficiently compact, portable, and automated to permit practical use.

Indicator dye/colorimetric methods are known that use indicator materials that undergo changes in color when water or alcohol is present in a storage tank with petroleum fuels. U.S. Pat. No. 4,699,885 to Melpolder and Victor describes a paste that undergoes a change in color when exposed to a water phase. This invention is only capable of detecting a distinct aqueous phase and is not capable of detecting water dissolved within petroleum fuels. U.S. Pat. No. 4,604,345 to Felder and Panzer describes a paste that undergoes a change in color when exposed to a phase of alcohol or to petroleum fuels containing dissolved alcohol. Any water dissolved within the petroleum fuel must be removed by a drying agent for the paste to properly indicate the presence of alcohol. Neither invention is capable of producing reproducible quantitative measurements of water or alcohol concentrations in petroleum fuels. U.S. Pat. No. 5,229,295 to Travis describes colorimetric tests for the presence of water and ethanol, and prescribes a separate step for the volumetric determination of alcohol concentration. Due to the reagent handling and restocking requirements, none of these methods is well-suited for the automated measurement of the water or alcohol content of petroleum fuels. While easy to use by a non-technically trained operator, the information gained by these inventions is very limited.

Several patents have been granted to inventions that incorporate humidity sensors into their design. Modern relative humidity sensors are composed of an interdigitated gold terminal on an alumina substrate overcoated with a thermosetting hydrophilic polymer. This polymer is a polyelectrolyte blend exhibiting a change in ionic mobility as water of hydration is absorbed. The ionic mobility is a direct function of the water vapor pressure in the ambient environment as well as the ambient temperature. The operating principle was patented by Martin Pope (Pope M., U.S. Pat. No. 2,728,831, 1955) though recent iterations of his invention have proven to yield sensors of greater stability.

According to Henry's Law, the partial pressure of water vapor in equilibrium with a solution phase is directly proportional to the moisture content of the solution provided the solution is sufficiently dilute. The partial pressure of water vapor is equal to the relative humidity (RH) multiplied by the saturated vapor pressure of water at any given temperature. To a good approximation, the solvent relative humidity (SRH) above any hydrophobic liquid is equal to the relative humidity (RH) in air in the absence of the vapors of that liquid.

Therefore, it is possible to determine the concentration of dissolved water for hydrophobic liquids by the equation:

$$C=(C_S)*(SRH/100\%)$$

where C=water concentration in ppm $C_S$=saturated water concentration in ppm at a given temperature and pressure SRH=solvent relative humidity as measured by the sensor The measurement of SRH can either be made in the head space above the liquid or within the liquid itself since the chemical potential of the water is a function of either the concentration of water or the water vapor pressure above the solution.

U.S. Pat. No. 6,138,674 to Gull and Hunt describes a module which measures the humidity of a patient's expired respiratory gases for the purpose of compensating for these variables in the delivery of gaseous anesthetic. U.S. Pat. No. 6,039,696 to Bell describes an adapter for the measurement of the humidity of inspired and expired gases in a patient with an artificial airway. The adapter may act as a control device to assist the delivery of ventilating gases with physiological levels of moisture. The apparatus also includes a display means which receives signals from the humidity sensor, translates the signals, and displays the results as percent relative humidity and/or moisture content. U.S. Pat. No. 6,347,746 to Dage et al. describes the incorporation of a humidity sensor into a system which monitors the temperature and humidity of air in a vehicle for the purpose of detecting and preventing conditions which lead to the fogging of vehicle windows.

Patents have been issued to inventions which determine the water content of materials by measuring the electrical properties of the materials and relating these properties to water content. U.S. Pat. No. 4,786,873 to Sherman describes a method to determine the water content of hydrocarbon-containing porous earth formations by measuring the dielectric permittivity of the earth formations. U.S. Pat. No. 3,966,973 to Henry et al. describes a process by which the moisture content of food is obtained by measuring the impedance generated by the food passing through an alternating current field. U.S. Pat. No. 6,388,453 to Greer describes a swept-frequency shunt-mode dielectric sensor system is used to measure complex impedance parameters such as capacitance and/or dielectric loss of particulate materials in order to calculate density and water content. U.S. Pat. No. 6,664,796 to Wang describes a process by which the moisture content of a fuel containing exclusively ethanol, and concentration of ethanol in the fuel, is obtained by measuring the resistance of the fuel. Many patents have been issued that employ sensors of dielectric properties to measure the water content associated with hydrocarbon liquids, especially crude oil. U.S. Pat. No. 5,070,725 to Cox et al. describes a water-cut meter which measures the impedance associated with crude oil and water mixtures. The percentage of water may be determined in both water continuous and oil continuous samples. U.S. Pat. No. 5,260,667 to Garcia-Golding et al. describes a method for determining the water content of oil-in-water emulsions by measuring the real part of a sample's specific admittance and by making corrections for the sample temperature. None of the above methods for determining the water content of petroleum samples yield information specifically concerning the dissolved water content, but only the water in a separate phase from the petroleum or emulsified with it.

Methods of determining water content in oil streams also include microwave technologies. U.S. Pat. No. 4,862,060 to Scott et al. and U.S. Pat. No. 5,389,883 to Harper determine water content from the frequency changes between emitted and received microwave signals caused by the dielectric properties of oil and/or water samples. These methods do not determine the dissolved water content of the petroleum samples. Furthermore, microwave technologies are often expensive to implement.

However, despite the above, a need still exists for a single, field-capable, test method which can be used to determine the amount of water in or degree of water saturation of non-aqueous liquids (whose detailed composition can be changed without notice) and assess the potential for such water to cause problems during the storage and use of these liquids.

SUMMARY OF THE PRESENT INVENTION

The present invention is directed toward the measurement of water or water-soluble liquids dissolved within non-aqueous liquids by the analysis of responses from an array of low cost sensors providing measurements of physicochemical properties.

Sensor responses to non-aqueous liquids are modeled and integrated to extract qualitative and quantitative information. The selection of sensors is based on the information desired, their sensitivities to physicochemical properties, and the practicality of their use.

In the preferred embodiment of this invention, sensors capable of providing information on the relative humidity, temperature, conductivity and capacitance are used to collect the information needed to identify the type or composition of the liquid present and then its water content. These data can be further processed to predict the relative water content of the liquid as it may either cool or warm. The liquid can then be given a rating which identifies the potential for water-related problems that are associated with the liquid such as the likelihood of forming separate phases based on temperature change. If a rating indicating a high potential for water-related problems is produced, the practitioner will be informed before or soon after the problem is manifest and suitable actions taken to remove the water before serious consequences can become manifest.

A particular complication found with some non-aqueous liquids, such as gasoline and diesel fuels, is that their chemical composition and resulting physicochemical properties constantly change due to the variability in the raw materials of their manufacture, the variability in processing procedures and parameters, and variability in the type and amounts of any blending chemicals added.

For instance, Federal and state laws may require the manufacture of gasoline that meets specific oxygen levels at different times of the year. Such requirements can be met through the use of various ethers or alcohols. The use of alcohols rather than ethers can have an enormous effect on the ability of the gasoline to dissolve water. K. Owen and T. Coley, "Oxygenated Blend Components for Gasoline," *Automotive Fuels Reference Book*, pp. 275-281, Society of Automotive Engineers, Inc., 1995. The present invention uses multiple physicochemical measurements to address the variability caused by changes in the composition and temperatures of these non-aqueous liquids to directly measure the water dissolved within these liquids.

Many sensor types may provide information about the system to be analyzed. The complementary response behaviors and sensitivities of sensors may be combined to construct an accurate representation of the physicochemical properties of interest. Many sensor types useful for this purpose are compact, reliable, and resistant to chemical degradation. Analytical instruments incorporating such arrays of sensors might also be highly compact, reliable, and durable. Such instruments can offer unique ease of use due to designs tailored for specific applications. A device of the invention might comprise sensors selected for their sensitivity to water dissolved within non-aqueous liquids, their signal transduction circuitry, a processing unit which applies an algorithm to the sensor measurement data, and some type of communication output, such as a visual display device, or an electrical transmission.

One application of the invention is the measurement of water dissolved within petroleum fuels. The contamination of fuels with water cannot usually be avoided and is, therefore, an issue of concern for the petroleum industry. Water dissolved within fuels decreases their quality and poses a corrosion threat to handling equipment. The corrosion of petroleum fuel handling equipment can result in the leakage of fuel and is a major cause of environmental damage. Fuels with a high water content burn poorly in combustion engines. As the fuel changes temperature, water may separate from the fuel causing combustion problems and may clog fuel filters. By monitoring the water in the fuel, the level of water can be kept at a low level, thereby avoid such storage and handling problems.

Another application of the invention is to avoid the addition of one batch of fuel to another where the combined fuel will have deleterious properties which neither of the original fuels possess. Each fuel has a specific tolerance to the presence of water that is based on its chemical composition. For example, when conventional gasoline becomes saturated with water, a two phase system will form consisting of water and gasoline where the water layer consists primarily of water and the gasoline is relatively unchanged. When an ethanol containing gasoline is saturated with water, a two phase system will also form but the water layer will contain mostly ethanol and the gasoline will be depleted in the ethanol resulting in a loss of octane rating. By providing a simple mechanism by which to readily identify the composition of a fuel and the amount of water present, a practitioner can prevent the mixing of fuels which, when combined, would produce a mixture that may prove unuseable depending upon the anticipated conditions of transportation, storage, and/or use.

For these reasons, it is desirable to monitor fuel stocks to determine their moisture content and composition.

Another application of the invention is the monitoring of a non-aqueous liquid to determine if unexpected changes have occurred. Here, a baseline of the expected or normal physicochemical properties is established. The properties are then monitored to determine if and when unexpected changes have occurred. If such changes occur, the liquid would undergo testing to ensure that no deleterious material has been added to the liquid.

BRIEF DESCRIPTION OF THE DRAWINGS

FIG. 1 depicts the relationship between the electrical resistance as determined by a humidity sensor and the solvent relative humidity of conventional gasoline at a series of temperatures.

FIG. 2 depicts the relationship between the electrical resistance as determined by a humidity sensor and the solvent relative humidity of 11% MTBE containing gasoline at a series of temperatures.

FIG. 3 depicts the relationship between the electrical resistance as determined by a humidity sensor and the solvent relative humidity of 10% ethanol containing gasoline at a series of temperatures.

FIG. 4 depicts the relationship between the oxygenate content and the dielectric constant of oxygenated gasoline at 20° C.

FIG. 5 depicts the relationship between the electrical resistance of the gasoline and the solvent relativity humidity of unoxygenated gasoline, and gasoline containing 1%, 3% and 10% ethanol.

FIG. 6 depicts the relationship between the electrical resistance as determined by a humidity sensor and the water content (vol %) of ethyl alcohol.

DETAILED DESCRIPTION OF THE INVENTION

In order to derive an accurate measurement of the moisture content of non-aqueous liquids, the responses from complementary sensors are combined. The specific choice of constituent sensors is based on performance characteristics, durability, cost, and other practical considerations. In general, multiple sensors are required to measure properties that depend on multiple factors. In the simplest case of a non-aqueous liquid of a predetermined composition, a single sensor sensitive to the presence of dissolved water may be used for the measurement of dissolved water content. However, if the composition of the non-aqueous liquid is unknown or variable, additional sensors are required to produce an accurate measurement of dissolved water content. A temperature sensor may also be used to increase the accuracy of the measurement if sensor responses vary with temperature.

The apparatus of the invention may therefore consist of a sensor array, sensor transduction circuitry, a processing unit, and electronic output for transmission to a display device. The sensor array is a combination of sensors which detect moisture, physical chemical properties, and temperature. The moisture sensor may be of many types including, but not limited to, polymer film resistive and capacitive sensors, infrared absorption sensors, and light refractive sensors. The chemical property sensor may be of many types including, but not limited to, capacitors of various geometries (e.g., a parallel-plate capacitor), interdigitated electrodes with or without film coatings, and sensors based on light refraction or absorption. The temperature sensor may also be of many types (e.g., mercury thermometers, thermistors, thermocouples). The following sensors and sensor combinations are suitable for use in the invention: moisture sensors, dielectric property sensors and temperature sensors; moisture sensors and dielectric property sensors; moisture sensors and temperature sensors; moisture sensors; dielectric property sensors and temperature sensors; and dielectric property sensors.

As one example of the application of the invention, a system for the measurement of water content within petroleum fuels is described below. The capacity of petroleum fuels to dissolve water depends on the content of oxygenating chemicals in the fuel (such as alcohols and ethers), the relative amounts of aromatic and paraffin hydrocarbons, and the temperature of the fuel. Thus, sensors sensitive to moisture, oxygenating chemicals, aromatic/paraffin hydrocarbons, and temperature are combined algorithmically to determine the moisture content of petroleum fuels. Petroleum fuels and solvents (e.g., gasoline, diesel, fuel oil, Stoddard solvent, and mineral spirits) may dissolve water until their saturation limits are reached, at which point the water will begin to form a separate layer, or phase.

The method comprises the collection of moisture, physical chemical properties, and temperature measurements and determining the dissolved water content or the likelihood that the petroleum fuel or solvent might undergo a phase separation from water. The water content can be determined as a mass concentration or as the solvent relative humidity (amount of water dissolved/maximum possible dissolvable amount×100%). A "letter grade" can then be assigned to the fuel based on the measurement. The letter grade which is assigned (indicative of the likelihood of phase separation) may be, for example, "A" through "E", where "A" would indicate very little danger of phase separation and "E" would indicate a high risk of phase separation.

Analysis of regular unleaded gasoline is an example of one application of the invention. PIANO (paraffins, isoparaffins, aromatics, naphthenes, and olefins) analysis (ASTM D 5443) of the fuel investigated showed the absence of oxygenating chemicals (e.g., alcohols and ethers). In order to re-create commercially available gasoline, oxygenating chemicals were blended into the gasoline. Methyl t-butyl ether (MTBE) was blended to simulate ether-containing gasoline. Ethanol was blended to simulate alcohol-containing gasoline. All reagents were dried thoroughly with zeolite molecular sieves. Water was introduced into the gasoline types by two different methods. For the unoxygenated gasoline and the MTBE-containing gasoline, dry portions of gasoline were mixed with portions of gasoline that were saturated with water. For the ethanol containing gasoline, aliquots of water were added to the gasoline.

Commercially available humidity sensors (EMD3000 and EMD4000, General Eastern) were used as moisture sensors. Electrical resistance of the gasoline samples was measured using these sensors when immersed in unoxygenated gasoline, MTBE-containing gasoline, and ethanol-containing gasoline. FIGS. 1, 2, and 3 depict the relationship between the sample electrical resistance determined by the humidity sensor and the solvent relative humidity of non-oxygenated, 11% MTBE containing, and 10% ethanol containing gasoline, respectively, at a series of temperatures. These measurements are also listed in Tables 1, 2, and 3, respectively:

TABLE 1

EMD3000 humidity sensor measurements in conventional gasoline

| Temperature (° C.) | Solvent Relative Humidity (%) | EMD3000 resistance (Ω) |
|---|---|---|
| 15 | 30 | 6,550,000 |
| 15 | 50 | 170,000 |
| 15 | 70 | 4960 |
| 15 | 90 | 1400 |
| 25 | 30 | 7,044,000 |
| 25 | 50 | 292,000 |
| 25 | 70 | 16,400 |
| 25 | 90 | 2870 |
| 35 | 30 | 12,400,000 |
| 35 | 50 | 900,000 |
| 35 | 70 | 106,000 |
| 35 | 90 | 14,400 |

TABLE 2

EMD3000 humidity sensor measurements in 11% MTBE gasoline

| Temperature (° C.) | Solvent Relative Humidity (%) | EMD3000 Resistance (Ω) |
|---|---|---|
| 5 | 30 | 24,450,000 |
| 5 | 50 | 446,000 |
| 5 | 70 | 11,400 |
| 5 | 90 | 1250 |
| 15 | 20 | 69,500,000 |
| 15 | 50 | 307,000 |
| 15 | 70 | 10,400 |
| 15 | 90 | 1210 |
| 25 | 30 | 14,100,000 |
| 25 | 50 | 448,000 |
| 25 | 70 | 14,500 |
| 25 | 90 | 1720 |

TABLE 3

EMD3000 humidity sensor measurements in 10% ethanol gasoline

| Temperature (° C.) | Solvent Relative Humidity (%) | EMD3000 resistance (Ω) |
|---|---|---|
| 5 | 31 | 30,600,000 |
| 5 | 46 | 1,030,000 |
| 5 | 62 | 102,000 |
| 5 | 77 | 20,100 |
| 5 | 92 | 7240 |
| 15 | 30 | 5,650,000 |
| 15 | 40 | 450,000 |
| 15 | 50 | 87,000 |
| 15 | 60 | 24,500 |
| 15 | 70 | 9500 |
| 15 | 80 | 4590 |
| 15 | 90 | 2670 |
| 25 | 18 | 17,100,000 |
| 25 | 36 | 165,000 |
| 25 | 55 | 13,060 |
| 25 | 73 | 2555 |
| 25 | 91 | 1008 |

In general, moisture measurements determined by the humidity sensor may be improved by correcting for the effects of temperature and chemical content such as oxygnating chemicals.

By measuring the temperature and physical chemical properties, the relationship between the eletrical resistance determined by the humidity sensor and the solvent relative humidity of the gasoline may be described by mathematical correlations. These correlations may be of any form. One form of correlation that describes the data is:

solvent relative humidity=$A \times \log(R) + B/\log(R)$, where R is the electrical resistance of the humidity sensor (Ω) and both A and B may be functions of temperature and chemical content. These functions may be of any form.

In the case of conventional gasoline, $A = -0.1607T + 0.634$, and $B = 8.7969T + 155.08$, where T is the temperature in degrees Celsius.

When ethanol (1-10 vol %) is the oxygenating chemical present, a good fit to data can be found with:

$A = -2.85$, and $B = [-5.4605 \log(\text{EtOH \%}) - 0.0496]T + [120.49 \log(\text{EtOH \%}) + 287.7]$, where EtOH % is the amount of ethanol blended with the gasoline (vol %).

When MTBE is the oxygenating chemical present, a good fit to data can be found with:

$A = 5.16\, e^{-6}T - 2.3091$ $B = -4.37\, e^{-4}T + 323.91$

This method of water content measurement can also be applied to the measurement of water dissolved in ethyl alcohol. FIG. 6 depicts the relationship between the electrical resistance of the humidity sensor and the solvent relative humidity of ethyl alcohol. These measurements are listed in Table 4:

TABLE 4

The relationship between the electrical resistance of the EMD4000 humidity sensor and the water content (vol %) of ethyl alcohol

| Water (vol %) | EMD4000 resistance (Ω) |
|---|---|
| 1 | 7050 |
| 10 | 3250 |
| 30 | 1420 |
| 50 | 877 |

The electrical properties of the gasoline were measured with a capacitor immersed within the gasoline. FIG. 4 depicts the relationship between the oxygenate content in gasoline and the dielectric constant measured from the capacitor at 20° C. (1 kHz frequency of excitation). Table 5 lists these measurements.

TABLE 5

Dielectric constant measurements of gasoline containing MTBE and ethanol, 20° C.

| Oxygenate vol % | Dielectric constant |
|---|---|
| MTBE: | |
| 0 | 2.06 |
| 5 | 2.15 |
| 11 | 2.25 |
| 15 | 2.30 |
| Ethanol: | |
| 0 | 2.06 |
| 2 | 2.15 |
| 5 | 2.32 |
| 7.5 | 2.50 |
| 10 | 2.78 |

For ethanol containing gasoline this relationship has been modeled as: oxygenate percentage=$A \times DC^2 + B \times DC + C$, where DC is the dielectric constant of the gasoline. A good fit to the data from ethanol-containing gasoline is possible when the following formulas for A, B, and C are used: $A = -0.0518\,T - 10.22$, $B = 0.2711\,T + 62.946$, and $C = -0.3244\,T - 86.643$, where T is the temperature (° C.). For MTBE containing gasoline, a good fit to the data can be achieved with the following formulas for A, B, and C: $A = 0$, $B = 0.3452\,T + 46.977$, and $C = -0.6520\,T - 98.125$, where T is the temperature (° C.).

Other mathematical relationships are possible. For greater accuracy, the effect of solvent relative humidity may be factored into the model of oxygenate content.

A capacitor was also used to measure the bulk electrical resistance (or conductance, equivalently) of the gasoline (20

Hz frequency or excitation). FIG. 5 depicts the relationship between the electrical resistance of the gasoline and the solvent relativity humidity for non-oxygenated gasoline, as well as 1%, 3% and 10% ethanol-containing gasoline. For a given oxygenate content, the electrical resistance of the gasoline decreases as the solvent relative humidity of the gasoline increases; Table 6 lists these measurements:

TABLE 6

Electrical resistance measurements of gasoline with varying amounts of ethanol and varying solvent relative humidity, 20° C.

| Solvent relative humidity (%) | Electrical resistance of test cell ($\Omega$) |
|---|---|
| Conventional: | |
| 0 | $1.56e^{10}$ |
| 50 | $9.36e^9$ |
| 100 | $5.12e^9$ |
| 1% ethanol: | |
| 0 | $5.26e^9$ |
| 17 | $4.89e^9$ |
| 50 | $3.82e^9$ |
| 84 | $2.82e^9$ |
| 100 | $2.14e^9$ |
| 3% ethanol: | |
| 0 | $1.49e^9$ |
| 22 | $1.13e^9$ |
| 44 | $8.02e^8$ |
| 67 | $5.74e^8$ |
| 89 | $3.13e^8$ |
| 100 | $2.14e^8$ |
| 10% ethanol: | |
| 0 | $3.51e^6$ |
| 19 | $2.43e^6$ |
| 48 | $1.39e^6$ |
| 76 | $7.16e^5$ |
| 100 | $3.61e^5$ |

Thus, the electrical resistance of the gasoline may provide water content information. One combination of measurements which yields the solvent relative humidity for ethanol containing gasoline is:

solvent relative humidity=$(A \times \log(Rc))+B$, wherein $A=(35.243 \times \log(EtOH\%))-135.87$, and $B=(-458.16 \times \log(EtOH\%))+1208.1$ where Rc is the electrical resistance ($\Omega$) of the capacitor immersed in gasoline and EtOH % is the amount of ethanol present in the gasoline (vol %). The concentration of aromatic hydrocarbons also influences the electrical properties of gasoline, including the dielectric constant and the conductivity of gasoline. Higher concentrations may yield larger dielectric constants and greater conductivities.

The resistance and capacitance measurements from a capacitor immersed in gasoline may provide oxygenate content and water content information. These measurements are considered duplicative to electrical impedance measurements (e.g., resistance and reactance) of a test cell containing the sample. Pairing a dielectric constant measurement with a phase angle difference from a measurement circuit may yield oxygenate content and water content information. Equivalent representations of the measurements may include, but are not limited to, susceptance capacitance, dielectric constant, complex permittivity, resistance, conductance, admittance, reactance and impedance. Furthermore, parameters derived from these property representations are considered to be equivalent representations of the measurement information.

Water tolerance is the amount of water that a non-aqueous liquid can dissolve before phase separation will occur with the formation of distinct non-aqueous and aqueous phases (the aqueous phase will also contain alcohols initially present in the solvent phase). Water tolerance is related to liquid relative humidity in that the water tolerance of a non-aqueous liquid is the concentration of water in the non-aqueous liquid at 100% relative humidity. In the case of petroleum fuels, water tolerance depends on factors such as temperature, type of distillate, content of blending components such as oxygenates, and aromatic hydrocarbon content.

With knowledge of how the water tolerance of a non-aqueous liquid varies with temperature, it is possible to predict its relative humidity (or the likelihood of phase separation occurring) at different temperatures. For example, if the relative humidity of a non-aqueous liquid was determined to be 50% at 30° C. and the water tolerance of the liquid were known to be 1 vol % at 30° C., then the water concentration would be estimated at 0.5 vol %. If the solvent were to cool to 10° C., and if the water tolerance of the liquid was 0.5 vol % at 10° C., then the relative humidity would be predicted to be at or near 100% and phase separation would be likely to occur.

Such determinations are useful when a fuel is to be transported, stored and/or used at different conditions from those of the initial measurement.

The temperature dependence of the water tolerance of conventional gasoline is estimated by the following correlation:

water tolerance, wt %=$6.97e^{-4}T+1.48e^{-2}$ where T is the temperature in ° C.

The temperature dependence of the water tolerance of gasoline containing 15 vol % MTBE is estimated by the following correlation:

water tolerance, wt %=$1.33e^{-3}T+5.96e^{-2}$ where T is the temperature in ° C.

The water tolerance of gasoline is greatly increased by blending with ethanol. The water tolerance of gasoline blended with ethanol can be estimated by the following correlation:

water tolerance, wt %=$aT^2+bT+c$ where $a=(-8.052e^{-8}(\%\ EtOH)^2)+(4.545e^{-6} \times (\%\ EtOH))+3.513e^{-6}$, $b=2.919e^{-5}(\%\ EtOH)^2+2.530e^{-4} \times (\%\ EtOH)+6.736e^{-4}$, $c=1.704e^{-3}(\%\ EtOH)^2+3.415e^{-2} \times (\%\ EtOH)+1.220e^{-2}$, where % EtOH is the amount of ethanol blended into the gasoline in vol % and T is the temperature in ° C.

What is claimed is:

1. A method for characterizing a liquid hydrocarbon fuel having unknown or variable composition, the method comprising:
   sensing the solvent relative humidity of the liquid hydrocarbon fuel;
   sensing the capacitance of the liquid hydrocarbon fuel;
   determining the amount of water or water-soluble compounds in said liquid hydrocarbon fuel,
      wherein determining the amount of water or water-soluble compounds includes comparing the solvent relative humidity, and the capacitance of said liquid hydrocarbon fuel to a plurality of pre-determined values of capacitance and solvent relative humidity of the liquid hydrocarbon fuel corresponding to a plurality of concentrations of water or water-soluble compounds in said liquid hydrocarbon fuel;

identifying which water-soluble compound or compounds are present in said liquid hydrocarbon fuel,
  wherein identifying which compound or compounds are present includes comparing the solvent relative humidity and the capacitance of said liquid hydrocarbon fuel to a plurality of pre-determined values of capacitance and solvent relative humidity of the liquid hydrocarbon fuel corresponding to a plurality of water-soluble compounds that may be present; and
calculating a temperature threshold for a water or water-soluble phase to form in said liquid hydrocarbon fuel during anticipated temperature conditions of transportation or storage based at least in part on said determining and identifying.

2. The method of claim 1, further comprising sensing the temperature of said liquid hydrocarbon fuel;
  wherein determining further includes a comparison of the temperature to a plurality of pre-determined values for temperature, capacitance and solvent relative humidity of the liquid hydrocarbon fuel corresponding to a plurality of concentrations of water or water-soluble compounds in said liquid hydrocarbon fuel; and
  wherein said identifying step further includes a comparison of the temperature to a plurality of pre-determined values for temperature, capacitance and solvent relative humidity of the liquid hydrocarbon fuel corresponding to a plurality of concentrations of water or water-soluble compounds in said liquid hydrocarbon fuel.

3. The method of claim 2, wherein said liquid hydrocarbon fuel is selected from the group consisting of: diesel fuel, fuel oil, marine diesel fuel, biodiesel fuel, gasoline, kerosene, jet fuel, ethanol, short-chain alkane fuel, and liquid petroleum gas.

4. The method of claim 2, further comprising the step of assigning a rating to said liquid hydrocarbon fuel based on said calculated temperature threshold for a water or water soluble phase to form.

5. The method of claim 1 wherein sensing the solvent relative humidity of said liquid hydrocarbon fuel further comprises sensing the humidity of said liquid hydrocarbon fuel.

6. The method of claim 1, further comprising the step of assigning a rating to said liquid hydrocarbon fuel based on said calculated temperature threshold for a water or water soluble phase to form.

7. The method of claim 1, wherein said liquid hydrocarbon fuel is selected from the group consisting of: diesel fuel, fuel oil, marine diesel fuel, bio-diesel fuel, gasoline, kerosene, jet fuel, ethanol, short-chain alkane fuel, and liquid petroleum gas.

* * * * *